(12) United States Patent  
Pfaff

(10) Patent No.: US 7,733,499 B2
(45) Date of Patent: *Jun. 8, 2010

(54) METHOD FOR OPTICALLY TESTING SEMICONDUCTOR DEVICES

(75) Inventor: Paul L. Pfaff, Lake Oswego, OR (US)

(73) Assignee: Attofemto, Inc., Lake Oswego, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/120,924

(22) Filed: May 15, 2008

(65) Prior Publication Data

US 2008/0252898 A1  Oct. 16, 2008

Related U.S. Application Data

(63) Continuation of application No. 11/278,389, filed on Mar. 31, 2006, now Pat. No. 7,400,411, which is a continuation of application No. 10/301,030, filed on Nov. 20, 2002, now Pat. No. 7,206,078.

(60) Provisional application No. 60/337,419, filed on Dec. 6, 2001.

(51) Int. Cl.
  *G01B 11/02* (2006.01)
  *G01B 9/021* (2006.01)
(52) U.S. Cl. .................. 356/503; 356/457
(58) Field of Classification Search .......... 356/457, 356/458, 481, 503, 504
See application file for complete search history.

(56) References Cited

U.S. PATENT DOCUMENTS

| 3,663,194 A | 5/1972 | Greenstein et al. |
| 3,956,698 A | 5/1976 | Malmberg et al. |
| 4,053,833 A | 10/1977 | Malmberg et al. |
| 4,242,635 A | 12/1980 | Burns |
| 4,355,278 A | 10/1982 | Burns et al. |
| 4,415,851 A | 11/1983 | Langner et al. |

(Continued)

OTHER PUBLICATIONS

H.K. Heinrich et al., "Noninvasive sheet charge density probe for integrated silicon devices," Appl. Phys. Lett. 48(16) Apr. 21, 1986, p. 1066-1068 with Errata, Appl. Phys. Lett. 48(26) Jun. 30, 1986, p. 1811.

(Continued)

*Primary Examiner*—Michael A Lyons
(74) *Attorney, Agent, or Firm*—Davis Wright Tremaine LLP; George C. Rondeau, Jr.

(57) ABSTRACT

A method for optically testing semiconductor devices or wafers using a holographic optical interference system with an infrared or thermal light source providing a light beam of coherent wavelength with a wavelength to which the semiconductor material is transparent, splitting the light beam into a reference beam and an object beam, imposing the object beam on the semiconductor material to generate a reflected object beam reflected from interior structures of the semiconductor material, adjusting the angle of the reference beam relative to the object beam between a plurality of angles with the semiconductor material being a different state for each angle of the reference beam, imposing the reflected object beam and the reference beam onto a detection device to create a plurality of interference patterns, one for each of the reference beam angles, and comparing the interference patterns to one another to determine and display characteristics within the semiconductor material.

16 Claims, 4 Drawing Sheets

U.S. PATENT DOCUMENTS

| | | | |
|---|---|---|---|
| 4,482,863 A | 11/1984 | Auston et al. |
| 4,554,453 A | 11/1985 | Feigt et al. |
| 4,618,819 A | 10/1986 | Mourou et al. |
| 4,681,449 A | 7/1987 | Bloom et al. |
| 4,703,260 A | 10/1987 | Beha et al. |
| 4,714,826 A | 12/1987 | Goutzoulis |
| 4,745,361 A | 5/1988 | Nees et al. |
| 4,758,092 A | 7/1988 | Heinrich et al. |
| 4,760,249 A | 7/1988 | Baskett |
| 4,786,864 A | 11/1988 | Beha et al. |
| 4,816,755 A | 3/1989 | Look et al. |
| 4,827,212 A | 5/1989 | Kamieniecki |
| 4,843,329 A | 6/1989 | Beha et al. |
| 4,868,492 A | 9/1989 | Beha et al. |
| 4,875,006 A | 10/1989 | Henley et al. |
| 4,881,029 A | 11/1989 | Kawamura |
| 4,896,109 A | 1/1990 | Rauscher |
| 4,933,634 A | 6/1990 | Cuzin et al. |
| 4,970,461 A | 11/1990 | LePage |
| 4,983,911 A | 1/1991 | Henley |
| 4,999,577 A | 3/1991 | Beha et al. |
| 5,034,683 A | 7/1991 | Takahashi et al. |
| 5,059,897 A | 10/1991 | Aton et al. |
| 5,216,359 A | 6/1993 | Makki et al. |
| 5,422,723 A | 6/1995 | Paranjpe et al. |
| 5,682,236 A | 10/1997 | Trolinger et al. |
| 5,999,152 A | 12/1999 | Liao et al. |
| 6,172,752 B1 | 1/2001 | Haruna et al. |
| 6,218,655 B1 | 4/2001 | Ogasawara et al. |
| 6,512,385 B1 | 1/2003 | Pfaff et al. |
| 6,803,777 B2 | 10/2004 | Pfaff et al. |
| 6,972,577 B2 | 12/2005 | Pfaff et al. |
| 7,206,078 B2 * | 4/2007 | Pfaff et al. ............ 356/517 |
| 7,323,889 B2 | 1/2008 | Pfaff et al. |
| 7,400,411 B2 * | 7/2008 | Pfaff ............ 356/503 |
| 2005/0231733 A1 | 10/2005 | Pfaff |
| 2006/0244974 A1 | 11/2006 | Pfaff |
| 2007/0019209 A1 | 1/2007 | Pfaff |

OTHER PUBLICATIONS

Ivanova et al., "Semiconductor Photographic System Based on High-Resistivity Gallium Arsenide," Soviet Physics—Semiconductors, vol. 6, No. 9, Mar. 1973, pp. 1585-1587.

B.J. Thompson, "Holographic Particle Sizing Techniques," J. Physics E: Scientific Instruments, vol. 7, pp. 781-788, 1974.

C.N. Kurtz, Holographic Polarization Recording with an Encoded Reference Beam, Applied Physics Letters 14(2), 59-61, 1969.

Dickson et al., Holographic Polarization-Separation Elements, Applied Optics 33(23) 5378-5385, 1994.

Saito et al., Solvent Vapour Method in Thermoplastic Photoconductor Media, J. Optics, 1980, pp. 285-292.

Rastogi and Pflug, Holographic Moire Phase Reinforcement Procedure to Obtain Variable Sensitivity Surface Topographical Mapping: Extension to Phase Stepping, Optics and Laser Technology 1992, vol. 24 (4), p. 203-207.

* cited by examiner

METHOD FOR OPTICALLY TESTING SEMICONDUCTOR DEVICES

CROSS REFERENCE TO RELATED APPLICATIONS

This application is a continuation of U.S. application Ser. No. 11/278,389, filed Mar. 31, 2006, now U.S. Pat. No. 7,400,411 which is a continuation of U.S. application Ser. No. 10/301,030, filed Nov. 20, 2002, now U.S. Pat. No. 7,206,078 issued Apr. 17, 2007, which claims the benefit of U.S. Provisional Application No. 60/337,419, filed Dec. 6, 2001.

BACKGROUND OF THE INVENTION

1. Field of the Invention

The present invention relates to non-invasive testing.

The development of advanced integrated circuit devices and architectures has been spurred by the ever increasing need for speed. For example, microwave, fiber optical digital data transmission, high-speed data acquisition, and the constant push for faster digital logic in high speed computers and signal processors has created new demands on high-speed electronic instrumentation for testing purposes.

2. Description of Related Art

Conventional test instruments primarily include two features, the integrated circuit probe that connects the test instrument to the circuit and the test instrument itself. The integrated circuit probe has its own intrinsic bandwidth that may impose limits on the bandwidth achievable. In addition, the probe also determines an instrument's ability to probe the integrated circuit due to its size (limiting its spatial resolution) and influence on circuit performance (loading of the circuit from its characteristic and parasitic impedances). The test instrument sets the available bandwidth given perfect integrated circuit probes or packaged circuits, and defines the type of electric test, such as measuring time or frequency response.

Connection to a test instrument begins with the external connectors, such as the 50 ohm coaxial Kelvin cable connectors (or APC-2.4). The integrated circuit probes provide the transitions from the coaxial cable to some type of contact point with a size comparable to an integrated circuit bond pad. Low-frequency signals are often connected with needle probes. At frequencies greater than several hundred megahertz these probes having increasing parasitic impedances, principally due to shunt capacitance from fringing fields and series inductance from long, thin needles. The parasitic impedances and the relatively large probe size compared to integrated circuit interconnects limit their effective use to low-frequency external input or output circuit responses at the bond pads.

Therefore, electrical probes suffer from a measurement dilemma. Good high-frequency probes use transmission lines to control the line impedance from the coaxial transition to the integrated circuit bond pad to reduce parasitic impedances. The low characteristic impedance of such lines limits their use to input/output connections. High-impedance probes suitable for probing intermediate circuit nodes have significant parasitic impedances at microwave frequencies, severely perturbing the circuit operation and affecting the measurement accuracy. In both cases, the probe size is large compared to integrated circuit interconnect size, limiting their use to test points the size of bond pads. Likewise sampling oscilloscopes, spectrum analyzers, and network analyzers rely on connectors and integrated circuit probes, limiting their ability to probe an integrated circuit to its external response. For network analysis, a further issue is de-embedding the device parameters from the connector and circuit fixture response, a task which grows progressively more difficult at increasing frequencies.

With the objective of either increased bandwidth or internal integrated circuit testing with high spatial resolution (or both) different techniques have been introduced. Scanning electron microscopes or E-beam probing uses an electron beam to stimulate secondary electron emission from surface metallization. The detected signal is small for integrated circuits voltage levels. The system's time resolution is set by gating the E-beam from the thermionic cathodes of standard SEM's. For decreasing the electron beam duration required for increased time resolution, the average beam current decreases, degrading measurement sensitivity and limiting practical systems to a time resolution of several hundred picoseconds. Also, SEM testing is complex and relatively expensive.

Valdmanis et al., in a paper entitled "Picosecond Electronics and Optoelectronics", New York: Springer-Verlag, 1987, shows an electro-optic sampling technique which uses an electrooptic light modulator to intensity modulate a probe beam in proportion to a circuit voltage. Referring to FIG. 1, an integrated circuit 10 includes bonded electrical conductors 12 fabricated thereon whereby imposing differential voltages thereon gives rise to an electric field 14. For carrying out a measurement an electro-opti needle probe 16 includes an electro-optic tip 18 ($LiTaO_3$) and a fused silica support 20. A light beam incident along path 22 is reflected at the end of the electro-optic tip 18 and then passes back along path 24. An electric field 14 alters the refractive index of the electro-optic tip 18 and thereby alters the polarization of the reflected light beam on the exit path 24, which thus provides a measure of the voltages on the conductors 12 at a single point. Unfortunately, because of the proximity of the probe 16 to the substrate 10 capacitive loading is applied to the circuit, thereby altering measurements therefrom. In addition, it is difficult to position the probe 16 in relation to the conductor because the probe 16 and circuit 10 are vibration sensitive. Also, the measurements are limited to conductors 12 on or near the surface of the circuit 10. Further, the circuit must be active to obtain meaningful results and the system infers what is occurring in other portions of the circuit by a local measurement.

Weingarten et al. in a paper entitled, "Picosecond Optical Sampling of GaAs Integrated Circuits", IEEE Journal of Quantum Electronics, Vol. 24, No. 2, February 1988, disclosed an electro-optic sampling technique that measures voltages arising from within the substrate. Referring to FIG. 2, the system 30 includes a mode-locked Nd:YAG laser 32 that provides picosecond-range light pulses after passage through a pulse compressor 34. The compressed pulses are passed through a polarizing beam splitter 36, and first and second wave plates 38 and 40 to establish polarization. The polarized light is then directed at normal incidence onto an integrated circuit substrate 42. The pulsed compressed beam can be focused either onto the probed conductor itself (backside probing) or onto the ground plane beneath and adjacent to the probed conductor (front-side probing). The reflected light from the substrate is diverted by the polarizing beam splitter 36 and detected by a single point slow photo diode detector 44. The photo diode detector is also connected to a display 46.

A microwave generator 48 drives the substrate 42 and is also connected to an RF synthesizer 50, which in turn is connected to a timing stabilizer 52. The pulse output of the laser 32 is likewise connected to the timing stabilizer 52. The output of the stabilizer 52 connects back to the laser 32 so that the frequency of the microwave generator 48 locks onto a frequency that is a multiple of the laser repetition rate plus an offset. As a consequence, one may analyze the electric fields produced within the integrated circuit as a result of being voltage drive, thus providing circuit analysis of the integrated circuit operation. In essence, the voltage of the substrate imposed by the microwave generator 48 will change the polarization in the return signal which results in a detectable change at the diode detector 44.

Referring to FIGS. 3A and 3B, the locations along the incident beam are designated a, b, c (relative to the "down" arrow), and designated along the reflected beam as d, e, and f (relative to the "up" arrow), and the intensity modulated output signal is designated as g. The corresponding states of polarization exhibited in the measurement process are shown in the similarly lettered graphs of FIG. 3B. At location a of FIG. 3A, the polarizing beam splitter 36 provides a linearly polarized probe beam (as shown in graph a of FIG. 3B) that is passed through the first wave plate 38, which is a T/2 plate oriented at 22.5 degrees relative to the incident beam polarization, so as to yield at location b the 22.5 degree elliptically polarized beam shown in graph b of FIG. 3B). The beam then passes through the second wave plate 40, which is a T/2 plate oriented at 33.75 degrees relative to the incident beam, so as to rotate the beam an additional 22.5 degrees to yield at location c the 45 degree polarization (shown in graph c of FIG. 3B), which is at 45 degrees to the [011] direction of the substrate 42, i.e., the cleave plane of the wafer. Similar rotations are shown for the reflected beam at the successive locations d, e, and f, the resultant polarizations respectively being as shown in graphs d, e, and f of FIG. 3B. As shown in graph f in particular, the electro-optic effect of any voltage present on the substrate 42 at the spot at which the beam reflects therefrom brings about a change in the specific polarization orientation in an amount designated in graph f of FIG. 3B as &, and that change is reflected in an amplitude change or intensity modulation in the output signal at location g that passes to the photo-diode 44 (as shown in graph g of FIG. 3B). It is the measurement of & that constitutes the voltage measurement. Among the various techniques of pre-determining the voltage patterns to be used in testing an integrated circuit, or indeed an entire printed circuit, Springer, U.S. Pat. No. 4,625,313, describes the use in a CPU of a ROM "kernel" in which are stored both a test program sequence and the testing data itself.

Since the system taught by Weingarten et al. does not include a probe proximate the circuit under test the limitations imposed by capacitive loading of the circuit to be tested is avoided. However, the system taught by Weingarten et al. is limited to "point probing," by the lens 41 converging the input beam into a test point on the order of one wavelength. Unfortunately, to test an entire circuit an excessive number of tests must be performed. In addition, it is not possible to test multiple points simultaneously without the use of multiple systems, which may be useful in testing different portions of the circuit that are dependant upon one another. The resulting data from the system is presented to the user as a single amplitude measurement, i.e., the intensity of the signal produced at the photo-diode 44 depends simply upon the degree to which the polarization of the reflected light entering the beam splitter 36 has been rotated, so that not only are the actual phase and polarization data that derive the reflection process lost, but the precision and accuracy of the measurement becomes subject to the linearity and other properties of the photo-diode 44 and the display 46.

Various other techniques by which semiconductors may be characterized, using electromagnetic radiation of different wavelengths under different conditions is cataloged by Palik et al. in "Nondestructive Evaluation of Semiconductor Materials and Device," Plenum Press, New York, 1979, chapter 7, pp. 328-390. Specifically, treatment is given of (1) infrared reflection of GaAs to obtain the optical parameters n and k and then the carrier density N and mobility u; (2) infrared transmission in GaAs to determine k from which is determined the wavelength dependence of free carrier absorption; (3) infrared reflection laser (spot size) scanning of and transmission through GaAs to determine free carrier density in homogeneity, including local mode vibrations; (4) far infrared impurity spectra; (5) infrared reflection and transmission from thin films on a GaAs substrate; microwave magnetoplasma reflection and transmission; (6) submillimeter-wave cyclotron resonance in GaAs to determine magnetotransmission; (7) ruby laser radiation to form a waveguide in a GaAs film on a GaAs substrate, the propagation features of which are then measured using infrared radiation; (8) infrared reflectance from multilayers of GaAs on a GaAs substrate; (9) reflectance measurements of graded free carrier plasmas in both PbSnTe films on PbSnTe substrates and InAs on GaAs substrates; (10) interferometric measurements of ion implanted layers; (11) infrared restrahlen spectra, also to determine lattice damage effects; (13) ellipsometric measurements of ion-implanted GaP; (14) determination of optical constants by internal reflection spectroscopy; (15) laser raster scanning of semiconductor devices to measure photoconductivity, to track the flow of logic in a MOS shift register (because of current saturation, the effect of the laser light differs in cells in the 0 or 1 logic state), and with a more intense laser power level to change those logic states (i.e., to write to the circuit); (16) laser raster scanning of semiconductor devices to determine variations in resistivity and carrier lifetimes; (17) thermal imaging of circuits to find hot spots; (18) Raman backscattering to determine free carrier density; (19) carrier injection to study the band edge; (20) birefringence measurements in monolayers of GaAs and AlAs on GaAs to characterize the resultant strain; (21) photoluminescence and cathodoluminescence measurements of implanted layers and acceptor and donor densities. With the exception of (7) above which relates to waveguide transmission, and also of (15) and (17), these techniques relate to the characterization of static systems. While (15) relates to a spot canning technique of the operational integrated circuit and (17) relates to hot-characterization of the device temperature.

BRIEF SUMMARY OF THE INVENTION

What is desired, therefore, is a high bandwidth non-invasive testing system for semi-conductor materials.

DETAILED DESCRIPTION OF THE INVENTION

Figure 1:
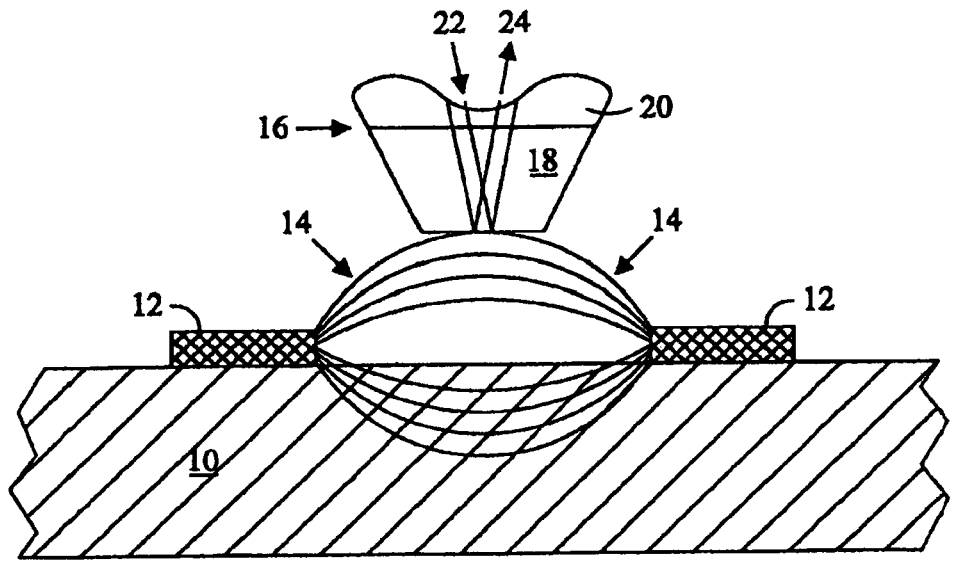
FIG. 1 illustrates an electro-optic sampling technique using electro-optic light modulator.
Figure 2:
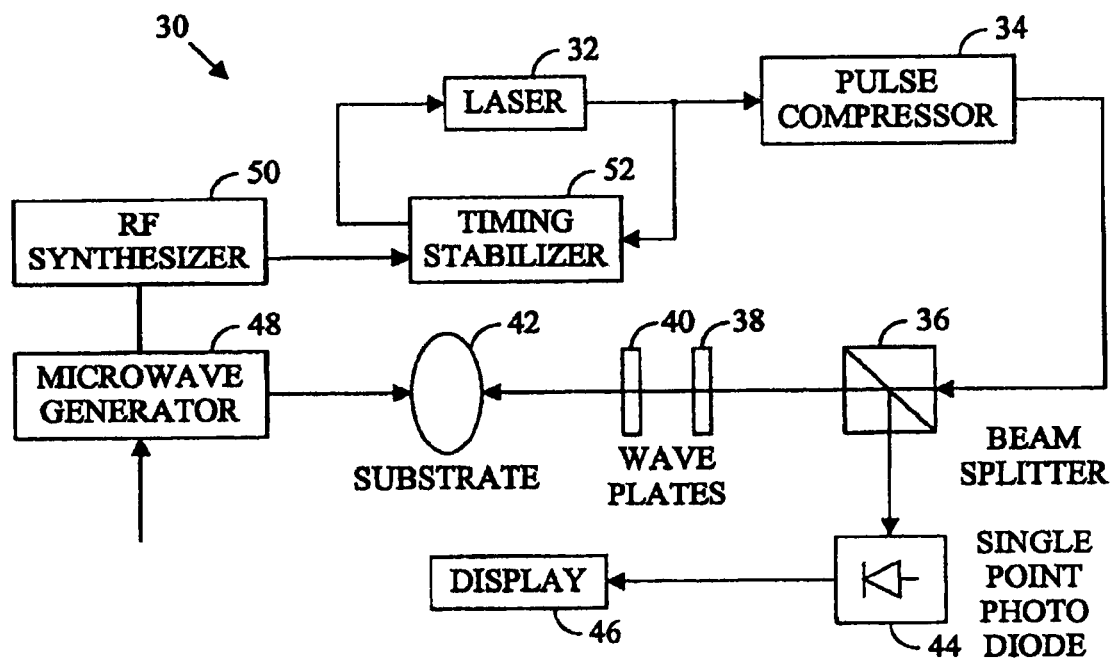
FIG. 2 illustrates a single point detection system.
Figure 3B:
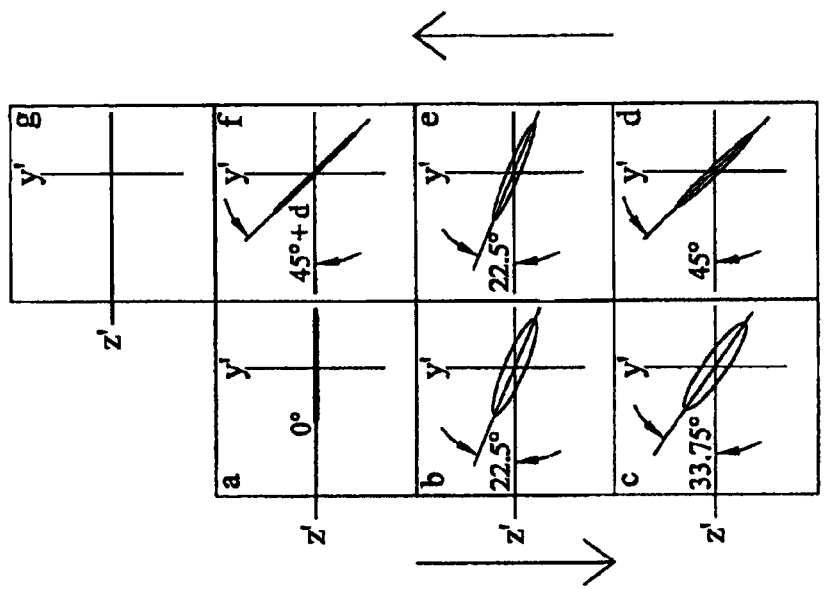
FIGS. 3A and 3B illustrate the beams of FIG. 2.
Figure 3A:
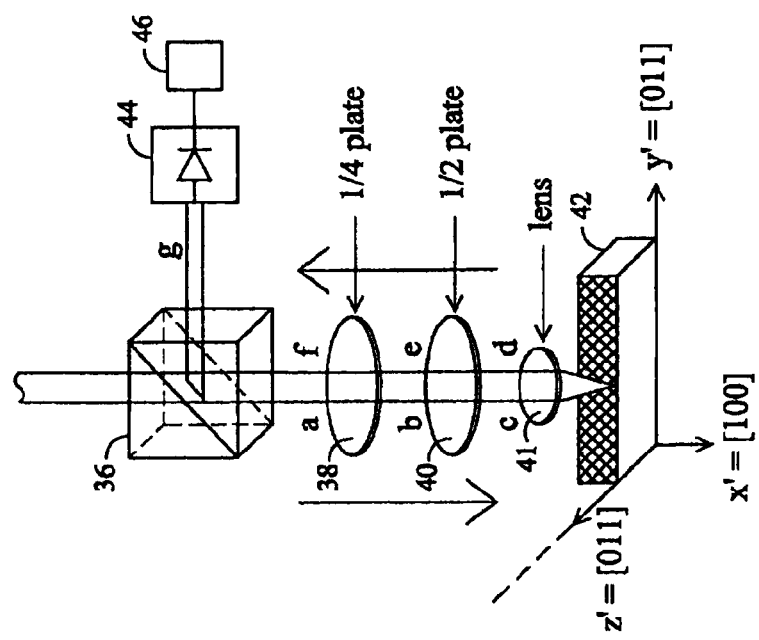

The present inventors came to the realization that the single point non-invasive probing technique of semiconductor materials could be enhanced if an area significantly greater than a wavelength of the optical test signal could be transmitted through or reflected off of a semiconductor material. Semiconductor materials generally exhibit electro-optic or photo-refractive effects, which can be made to become birefringent by the application of an electric field, either as such or as embodied in electromagnetic radiation. The present inventors then came to the realization that if an object in a state in which it is not birefringent, but such birefringence can then be brought about by electrical or electromagnetic techniques, the nature of the birefringence so introduced can be studied to determine characteristics of the material. Upon further consideration the present inventors then came to the realization that interferometry techniques can sense a wide region, such as that passing through or reflected off a semiconductor material, which can then be analyzed.

An interference pattern is created by a coherent light beam being transmitted through or reflected from an object onto a recording medium or otherwise a sensing device, which at the same time the original beam is also directed onto that recording medium or otherwise sensing device as a reference beam. Various characteristics of the resultant transmitted or reflected beam, herein called the "object wave," are recorded in the resultant interference pattern between the object wave and the reference beam. That is to say, inasmuch as the intensities of the reference beam and the object wave have been recorded in that interference pattern, the resulting pattern typically includes a set of fringes as a result of the applied voltage. Those characteristics are in part a consequence of the physical structure (i.e., "appearance") of the object, hence the interference pattern is related to the structure of the object.

The present inventors also realized that particular semiconductor materials are generally transparent to light of particular wavelengths so that the light may freely pass through and reflect back though the semiconductor, or otherwise pass through the semiconductor, substantially unaffected when the semiconductor is not stressed, such as by no applied voltage. Likewise, when the semiconductor material, such as an integrated circuit, is stressed by applying a voltage therein by energizing a circuit fabricated therein, the same light will reflect or otherwise pass through the semiconductor material, while being affected by the changes imposed by the applied voltage, such as birefringence, thereby resulting in a different pattern. The stressed and unstressed states can be recorded as different interferometry images. The two interferometry images may then be compared to one another to determine the actual operating characteristics within the semiconductor material. Also, two different stressed states of the semiconductor material may be obtained and thereafter two interferometry images, both from stressed states, may be compared to one another. In addition, by its nature, interferometry techniques record a significant spatial region much larger than a single wavelength simultaneously which is important for characterizing regions of the semiconductor material. For example, the operational characteristics of two different regions may be interrelated which is unobtainable using techniques limited to a single wavelength in "spot size." The present inventor's realization that the application of interferometry techniques for the testing of semiconductor devices was only after at least the culmination of all of the aforementioned realizations.

Of particular interest is the "real time" characterization of operating characteristics of integrated circuits where such birefringence is introduced by the electro-optic effect, i.e., the imposition of a voltage onto the object (as in the ordinary operation of the integrated circuit) causes birefringence therein. In other words, upon application of an electric field the material, such as GaAs or silicon, introduces an anisotropy and the ordinary complex refractive index n* of the material is decomposed into $n_o^*$ and $n_e^*$ components. Another technique applicable to appropriate substrates whether or not any operational voltages are also applied thereto, lies in utilization of the photo-refraction effect, wherein electromagnetic radiation of a required intensity is illuminated onto the substrate, and a birefringence or change in birefringence is then brought about. Inasmuch as semiconductor and like materials are generally characterized by a wavelength threshold below which photo-refraction will occur, but above which no photo-refraction takes place, this latter mode of operation employs electromagnetic radiation of differing wavelengths, first to bring about a desired photo-refractive effect, and then secondly to analyze the effect so brought about.

Figure 4:
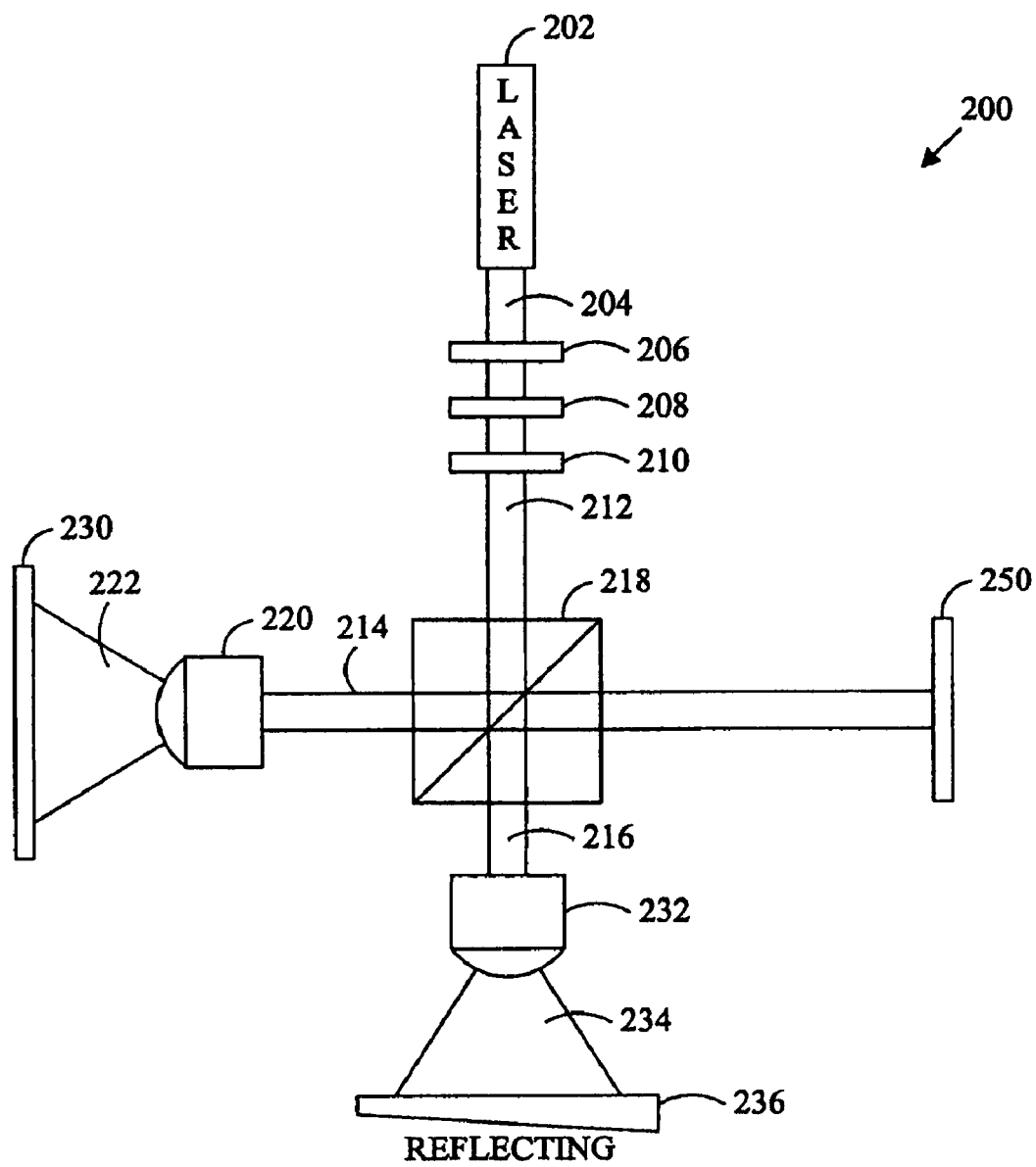
FIG. 4 illustrates one optical system for non-destructive wave front testing of a device under test.

FIG. 4 shows an interferometry apparatus 200 comprising a laser 202 such as a infrared DFB laser diode or the like, from which is derived a plane wave of linearly polarized light 204. The optical path thus defined may optionally include a selected first neutral density filter 206 that permits convenient adjustment of the laser power level. Likewise, the beam intensity may be varied by the applied voltage level. The beam 204 from the laser 202 (or from the filter 206, if used) may then be passed into a first broad band polarization rotator 208 for purposes of placing the plane of polarization of the laser beam at a desired orientation. Whether or not the polarization rotator 208 is used, the beam may then be passed through one or more first wave plates 210 that may optionally be used to establish a desired degree of ellipticity in the beam. Further, the wave plates may likewise establish with the beam is non-diverging/non-converging, diverging, or converging. In any case, the resultant beam 212 is then separated into a pair of beams 214 and 216 by a beam splitter 218. The beam splitter 218 may alternatively be any device suitable to separate the beam 212 into multiple beams. Likewise, components or beams 214 and 216 are interchangeable.

The beam 214 may pass through a first lens 220 that will then yield an expanded and/or expanding plane wave 222. The plane wave 222 is then incident on a device under test 230. The plane wave 218, having a wavelength suitable to pass through semiconductor material, passes through either the front side or the back side (or the edge) of the surface of the device under test 230 and reflects from the interior structures within the device under test 230. As a result of beam 222 being reflected back from the device under test 230, the reflected beam will pass back onto beam splitter 218 so as to be passed towards and ultimately impinge upon a recording device 250. The recording device 250 may be any suitable type of sensing device, such as for example, a charge coupled device.

Similarly, the beam 216 may pass through a second lens 232 that will then yield an expanded and/or expanding plane wave 234. The plane wave 234 is then incident on a reflecting device 236. The plane wave 218, having a wavelength suitable to pass through semiconductor material, reflects from a reflecting device 236. As a result of beam 234 being reflected back from the reflecting device 236, the reflected beam will be reflected by the beam splitter 218 so as to be passed towards and ultimately impinge upon the recording device 250.

Since both the reference beam (second beam 234) and the object beam (object beam 222) derive from a common, preferably coherent source (laser 202) and are simultaneously, or substantially simultaneously, incident on the recording device 250, the favorable conditions for forming an interference pattern are present. One or more of the lenses may be omitted, as desired. Also, the object and reference beams may be reversed relative to the beam splitter, as desired. It is likewise to be understood that one or more light sources may be used, as desired. Also, it is to be understood that more or more recording devices may be used, as desired. In addition, it is to be understood that the recording device(s) may record the object beam and the reference beam independently of one another, which are thereafter combined in a suitable manner to generate an interference wave front pattern.

For purposes of the present invention, and in taking an initial interference, the device under test may be any suitable device to which the characteristics are desired, such as for example, a functional integrated circuit on which the surface has been exposed (i.e., potting is not present) but to which no voltages or other external stimuli have been applied, a semiconductor material such as a wafer taken from or existent within a wafer manufacturing line, a semiconductor wafer taken from or existent within a chip manufacturing line at any of various stages of manufacture (deposition, etching, metallization, etc.) or the like, the recording device may be taken to be any suitable material for recording or otherwise sensing an interference image, such as for example, a photographic film, charge coupled device, or thermoplastic plate onto which the initial interference pattern is recorded in the graphic film, charge coupled device, or thermoplastic plate onto which the initial interference is sensed and/or recorded.

As to the case in which the device under test is a functional but not energized integrated circuit, a first interference may be recorded therefrom using the apparatus as shown in FIG. 4, i.e., the interference pattern is recorded either onto photographic film, charge coupled device, or within a thermoplastic plate. A second interference may then be made of that same to recording device while either being energized with a voltage or current, or illuminated with light of a wavelength shorter than the characteristic threshold wavelength for the material. In the case in which the device under test is a semiconductor wafer, a first interference may similarly be recorded/sensed and then a second interference may be recorded/sensed while illuminating the wafer in the manner just stated. In either case, any birefringence effects brought about either by the electro-optic effect or by the photo-refractive effect will then be recorded/sensed. A comparison of the two interferences, both taken from one or the other instance of the device under test, will isolate such electro-optically or photo-refractively produced birefringence.

It is preferred to employ a CCD camera as the sole recording device whereby the first and indeed a multiplicity of subsequent interference patterns may be recorded, at rates commensurate with the rates of operation of an integrated circuit itself, i.e., 50 MHZ or more in terms of charge coupled device operation. An additional advantage in using only the CCD camera for recording interference is that the "reference" interference, i.e., the interference recorded from the device under test (either as an IC or as a semiconductor wafer) at a time that no voltages or birefringence-inducing laser light was applied thereto, will be recorded digitally as well, and comparisons between the reference and subsequent interferences may be made by means other than within the experimental apparatus itself. i.e., by ordinary digital signal processing (DSP).

For the purpose of processing such a data stream an analyzer connected to the recording device, and then a monitor connecting to analyzer. Inasmuch as the laser source in the present embodiment is preferably a DBF infrared laser diode (e.g., 900 nm-1600 nm, or 1000 nm-1500 nm, or 2000 nm-14, 000 nm), the data to be analyzed may be generated by means of triggering the recording of CCD images in synchrony with the imposition of particular voltage data onto the test object, which may be an IC or possibly an entire printed circuit. As noted previously, the Springer patent describes the use of a digital "kernel" comprising a predetermined test program together with the digital data to be employed by that program, both of which are stored in ROM. The Springer apparatus then uses voltage probes and the like applied to various circuit nodes to test circuit performance in a "manual" fashion; the present invention, of course, in addition permits an "automatic" process of testing an entire IC, circuit board or a semiconductor wafer at any desired stage of manufacture.

During operation a first interference pattern, stressed or unstressed, may be obtained with the "fringes" around a particular feature of interest identified. With changes in the applied voltage and/or field the location and/or density of the fringes will vary. However, with slight changes in the fields the exact applied field and/or voltage may be difficult at times to determine. The determination may be assisted by understanding the material's optical properties and physical characteristics (e.g., thickness, layout, doping profile, shape, etc.). Accordingly, the reflecting device 236 may include an adjustment mechanism to vary the location and/or angle of the reflecting device 236 with respect to the beam incident thereon. By varying the position of the reflecting device 236 the location of the fringes may be modified, such as to line up with respect to a feature, such as a conductor. Thereafter a second interference pattern, stressed or unstressed, may be obtained with the "fringes" around a particular feature of interest identified. The change in the fringes between the two states, together with known characteristics of the particular materials within the device under test in the region of interest, may be used to determine the voltage or relative voltage change within the material in the region of interest. Similarly, the change in the wave front fringes between the two states, together with known voltages or relative voltage change, may be used to characterize the particular materials within the device under test in the region of interest. The change in the wave front fringes may be determined, for example, by subtraction, by addition, or any other suitable image comparison operation. It would likewise be noted that many such operations, such as subtraction, are capable of resolving features less than one wavelength in size. In addition, changes in the wave front fringes with known devices, using VLSI or VHDL circuit coordinate maps (or the like) may be used to characterize voltages and voltage changes. This permits for the observation of voltages within individual devices such as transistors or analysis of device registers or individual values of larger structures such as a micro-controller, or characterize fringes within the doped and non-doped conductive, semi-conductive, and non-conductive material (e.g., dielectric material) adjacent conductors, non-conductors, or semi-conductor material, or the like. Also, this technique may be used to study the effects of incident radiation, such as radio waves, x-rays, magnetic fields, chemical solutions upon the materials, etc.

It will be understood by those of ordinary skill in the art that other arrangements and disposition of the aforesaid components, the descriptions of which are intended to be illustrative only and not limiting, may be made without departing from the spirit and scope of the invention, which must be identified and determined only from the following claims and equivalents thereof.

Figure 5:
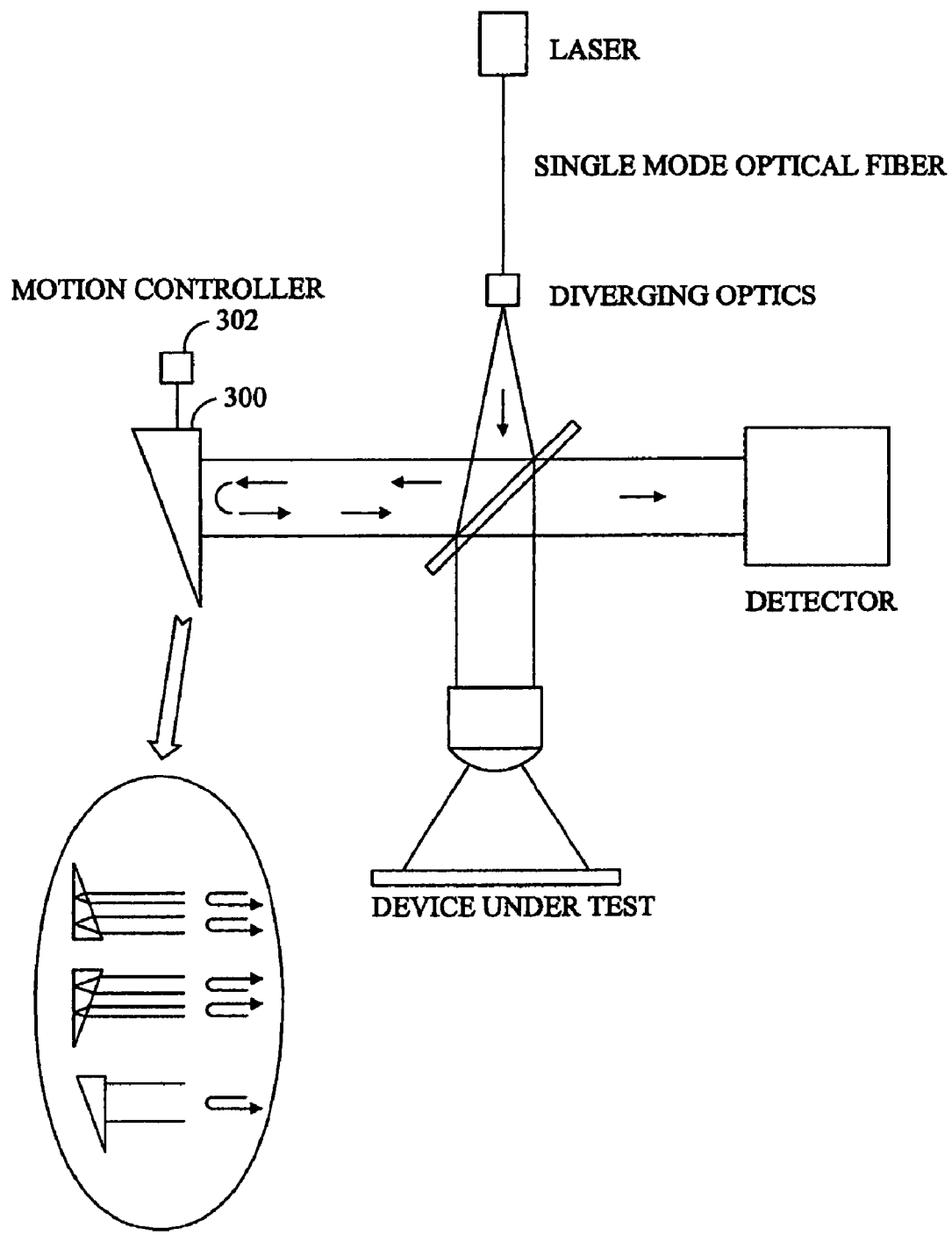
FIG. 5 illustrates another optical system for non-destructive wave front testing of a device under test.

Referring to FIG. 5, another alternative design for the optical system is illustrated for introducing an additional spatial shifting feature to the system. In the reference beam path an spatial beam adjustment member 300 is included. The spatial beam adjustment member 300 spatially offsets the reflected beam relative to the incident beam. In addition, the spatial beam adjustment member 300 may likewise be adjustable to any suitable angle. By recording the interference patterns at multiple different angles, for the same object beam, and processing the same as previously described you may obtain parallax information. In essence, this parallax information provides some three-dimensional information with respect to the structure and voltages within the device under test.

The invention claimed is:

1. A method for optically testing and displaying internal stresses of semiconductor devices or wafers while being manufactured, the device or wafer under test being comprised a semiconductor conductor material having an interior surface and interior structures, comprising:
   using a holographic optical interference system with at least one light source providing at least one light beam of coherent wavelength with a wavelength to which the semiconductor material is at least semi-transparent or transparent, splitting the light beam into a pair of beams, comprising a reference beam and an object beam, imposing the object beam on the exterior surface of the semiconductor material to generate a reflected object beam reflected from the interior structures of the semiconductor material, to generate a reflected beam reflected from the interior structures of the semiconductor material, adjusting the angle of incidence of the reference beam relative to the object beam between a plurality of angles with the semiconductor material being in a different state for each angle of the reference beam, imposing the reflected object beam and the reference beam onto a one or more detection devices to create a plurality of interference patterns of the reflected object beam with the reflected reference beam, one interference pattern at each of the plurality of angles of the reference beam, wherein the detection device or devices physically records or digitally stores the plurality of interference patterns, and comparing the plurality of interference patterns to one another to determine and display stress and interior structure characteristics within the semiconductor material, device or wafer.

2. The method of claim 1, wherein at least one of the states of the semiconductor material is an external stress, the external stress being produced by imposing incident electric or electromagnetic field or signals upon the semiconductor material or device.

3. The method of claim 1, wherein at least one of the states of the semiconductor material is an external stress, the external stress being produced by imposing incident voltages or chemical solutions upon the semiconductor material or device.

4. The method of claim 1, wherein at least one of the states of the semiconductor material is an external stress, the external stress being produced by imposing incident radio waves upon the semiconductor material or device.

5. The method of claim 1, wherein at least one or more detector devices records a plurality of interference patterns of a plurality of one or more external stresses which produce a change in the state of the refractive indexes or birefringence states of the semiconductor material or device.

6. The method of claim 5, wherein at least one of the states of the semiconductor material is a plurality of one or more external stresses are caused being produced by imposing a plurality of electromagnetic radiation stresses of one or more beams of differing wavelengths shorter than the characteristic threshold for the semiconductor material or device.

7. The method of claim 5, wherein at least one of the states of the semiconductor material is an external stress detected by means of triggering the recording or storage device of a plurality of interference patterns in synchrony with the imposition of a plurality of one or more external or internal stresses or electromagnetic signals or external stresses acting upon the semiconductor material or device.

8. The method of claim 5, wherein one or more beams incident to the semiconductor material or device and the interference pattern of each beam are recorded or detected by one or more recording or detector devices.

9. The method of claim 1, wherein the angles of the reference beam is adjusted to be converging or diverging to the object beam to enhance the visibility or contrast of the interference pattern with respect to a feature of the semiconductor material or device.

10. The method of claim 9, wherein automatic digital signal or image processing the plurality of interference patterns process and displays the plurality of internal stresses within the semiconductor material or feature or wafer at any desired stage of manufacture.

11. The method of claim 9, wherein the detection device records or digitally stores changes in the plurality of interference patterns to characterize and display at least one internal stress.

12. The method of claim 9, wherein the interference patterns are compared by digital signal or image processing with an electronic circuit coordinate map to determine and display at least one internal stress of a feature or an interior surface or structures within the semiconductor materials or external stress or stresses acting upon the semiconductor materials or wafer.

13. The method of claim 12, wherein the comparison of one or more interference patterns displays internal stresses and operating characteristics of features within the feature or interior structures or internal surfaces of the semiconductor material or wafer.

14. The method of claim 12, wherein by recording or comparing the interference pattern of at least one or more stresses acting upon the semiconductor material or wafer the interferometric pattern or patterns of differing stress states is determined or displayed.

15. The method of claim 12, wherein by recording at least one or more interference patterns of at least one or a plurality of internal stresses recorded at one or more different angles, for the same object beam, a plurality of interference patterns is obtained or displayed of at least one or a plurality of internal stresses within the semiconductor material or wafer.

16. The method of claim 15, wherein analysis of the plurality of interference patterns recorded at different angles generates two- or three-dimensional information of at least one internal stress acting upon an exterior surface or interior structures or feature within the semiconductor material or wafer.

* * * * *